United States Patent [19]
El Ghoul et al.

[11] Patent Number: 5,539,091
[45] Date of Patent: Jul. 23, 1996

[54] N-ALKYL, N-ACETYLGLYCOSYLAMINES

[75] Inventors: Mustapha El Ghoul, Toulouse Cedex; Patricia Latge, Brives; Isabelle Rico; Armand Lattes, both of Ramonville; Lionel Godefroy, Moirans, all of France

[73] Assignee: Stepan Europe, France

[21] Appl. No.: 213,858

[22] Filed: Mar. 16, 1994

Related U.S. Application Data

[63] Continuation of Ser. No. 110,482, Aug. 20, 1993, abandoned, which is a continuation of Ser. No. 795,122, Nov. 20, 1991, abandoned.

[30] Foreign Application Priority Data

May 22, 1991 [FR] France ................... 91 06175

[51] Int. Cl.$^6$ ............... C07H 5/04; A61K 31/70
[52] U.S. Cl. ........................................ 536/22.1
[58] Field of Search .............. 536/22.1, 53; 514/42

[56] References Cited

U.S. PATENT DOCUMENTS

| | | | |
|---|---|---|---|
| 4,631,272 | 12/1986 | Lockhoff et al. | 514/23 |
| 4,737,488 | 4/1988 | Lochoff et al. | 514/42 |
| 4,891,425 | 1/1990 | Lcokhoff et al. | 536/22 |

OTHER PUBLICATIONS

Doctoral Thesis of Patricia Latge at University of Paul Sabatier, "Nouveaux Tensioacites Derives du Lactose: Synthesis and Applications", 1990.

J. G. Erikson, J. Am Chem. Soc. 77:2839–2843 (1955) "Reactions of Long Chain Amines. V. Reactions with Sugars".

Latge et al., J. Dispersion Science & Technology 12: 227–233 (1991) "Synthesis of Long Chain N–Alkyllactylamines from Uprotected Lactose A New Series of Non-–Ionic Surfactants".

*Primary Examiner*—Gary L. Kunz
*Attorney, Agent, or Firm*—Banner & Allegretti, Ltd.

[57] ABSTRACT

The invention relates to N-alkyl, N-acetylglycosylamines of the formula:

$$\begin{array}{c} COCH_3 \\ | \\ R_1-N-R_2 \end{array}$$

wherein $R_1$ represents the residue of a reducing sugar selected from among glucose, galactose, lactose, or cellobiose;

$R_2$ is an alkyl radical, either linear or branched, comprising from 1 to 24 atoms of carbon, preferably from 8 to 18 atoms of carbon, under the reservation that, when $R_1$ is a residue of lactose, that $R_2$ is then different from the nonyl radical. These compounds are useful as surfactants.

10 Claims, 1 Drawing Sheet

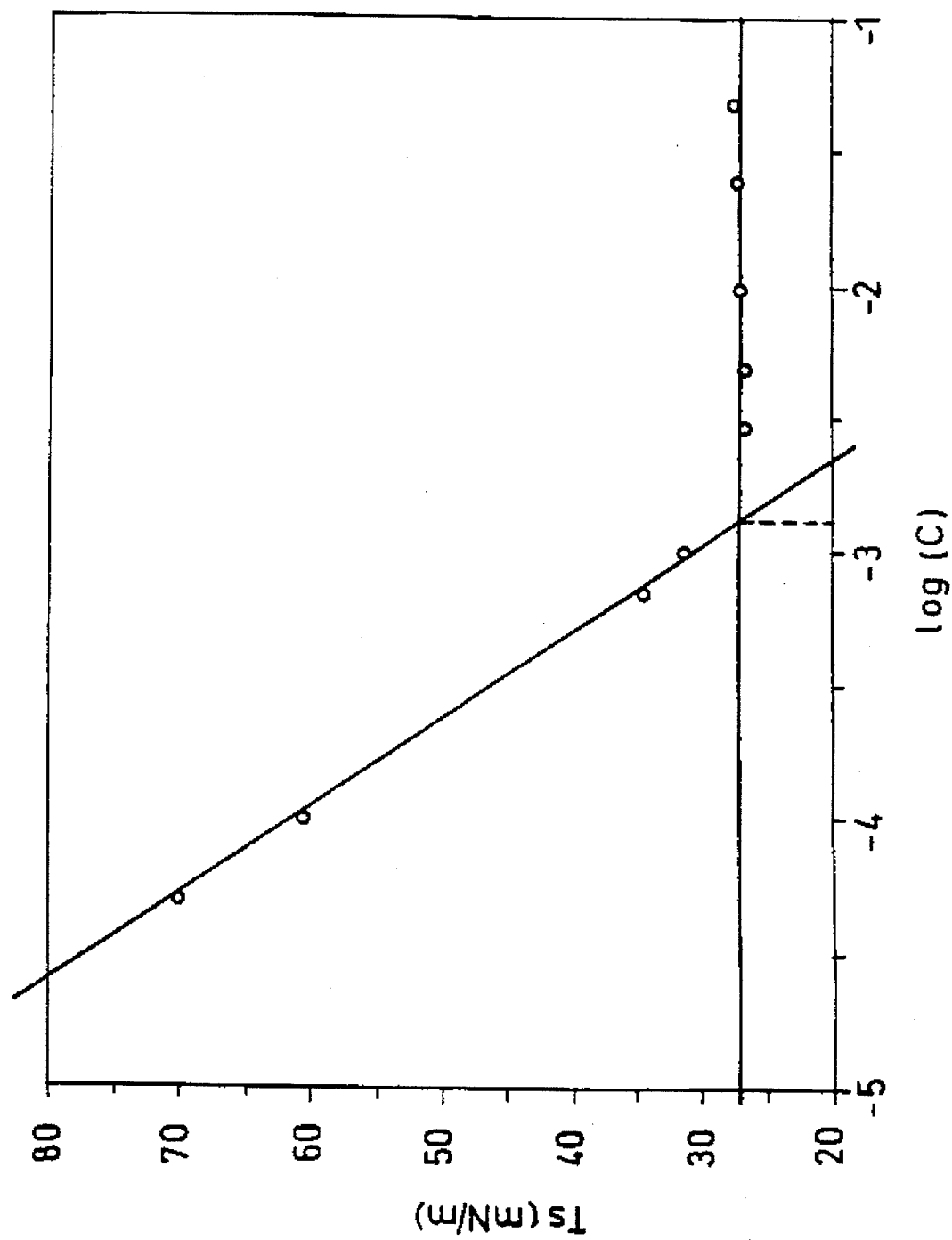

N-ALKYL, N-ACETYLGLYCOSYLAMINES

This application is a continuation of U.S. application Ser. No. 08/110,482, filed Aug. 20, 1993, now abandoned, which is a continuation of U.S. application Ser. No. 07/795,122, filed Nov. 20, 1991, now abandoned.

BACKGROUND OF THE INVENTION

1. Field of the Invention

This invention relates to long-chain N-alkyl, N-acetylglycosylamine derivatives, a process for their preparation, and their use, particularly as surface-agents (surfactants).

2. Description of the Related Art

The synthesis of N-alkylglycosylamines is described in J. Am. Chem. Soc. 77: 2839, Erickson, 1955.

SUMMARY OF THE INVENTION

The present invention provides new surface-active agents (surfactants) that are prepared starting from monosaccharides or reducing disaccharides, such as, in particular, glucose, galactose, lactose or cellobiose.

In fact, the act of grafting a long chain alkyl group onto these sugars, which are first aminized, makes it possible to obtain surface-active agents with chiral polar heads, which are relatively non-toxic.

However, because the resulting N-alkylglycosylamines are unstable in aqueous solution, the N-alkylglycosylamine derivatives can only be used directly as surface-active agents. It has now been found unexpectedly that acylation of the N-alkylglycosylamines improves their stability in aqueous solution, while still preserving their surface-active properties.

The invention thus has as its object N-alkyl, N-acetylglycosylamine derivatives of Formula I:

wherein $R_1$ represents the residue of a reducing sugar selected from among glucose, galactose, lactose, or cellobiose;

$R_2$ is an alkyl radical, either linear or branched, comprising from 1 to 24 atoms of carbon.

BRIEF DESCRIPTION OF THE DRAWING

FIG. 1 is a graph of surface tension versus the log of the concentration of N-decyl, N-acetylglycosylamine.

DETAILED DESCRIPTION OF THE INVENTION

The present invention provides new surface-active agents that are prepared starting from monosaccharides or reducing disaccharides, such as, in particular, glucose, galactose, lactose or cellobiose.

In fact, the act of grafting a long alkyl chain onto these sugars, which are first aminized, makes it possible to obtain surface-active agents with chiral polar heads, which are relatively non-toxic.

However, because the resulting N-alkylglycosylamines are unstable in aqueous solution, the N-alkylglycosylamine derivatives can only be used directly as surface-active agents. It has now been found unexpectedly that acylation of the N-alkylglycosylamines improves their stability in aqueous solution, while still preserving their surfactant properties.

The invention thus has as its object N-alkyl, N-acetylglycosylamine derivatives of Formula I:

wherein $R_1$ represents the residue of a reducer sugar selected from among glucose, galactose, lactose, or cellobiose;

$R_2$ is an alkyl radical, either linear or branched, comprising from 1 to 24 atoms of carbon.

The derivatives of Formula I are new products, under the proviso that, when $R_1$ is a residue of lactose, $R_2$ is not nonyl.

The invention advantageously relates to derivatives of Formula I, in which $R_1$ is the residue of a glucose, that is to say, the derivatives of Formula II:

wherein $R_1$ is an alkyl radical, either linear or branched, comprising 1 to 24 atoms of carbon.

Other advantageous derivatives are the derivatives of Formula I, in which $R_t$ is the residue of a lactose, such as represented by the Formula III:

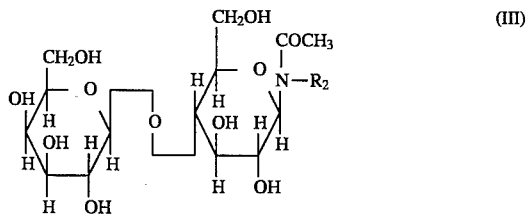

wherein $R_2$ is an alkyl radical, either linear or branched, comprising 1 to 24 atoms of carbon, with the exception of the nonyl radical.

The derivatives of formulas I, II and III, in which $R_2$ is an alkyl radical, either linear or branched, comprising from 8 to 18 atoms of carbon, are particularly preferred.

The N-alkyl, N-acetylglycosylamines of Formula I may be prepared through the acylation of the corresponding N-alkylglycosylamines of Formula IV:

wherein $R_1$ represents the residue of a reducer sugar selected from among glucose, galactose, lactose, or cellobiose;

$R_2$ is an aklyl radical, either linear or branched, comprising from 1 to 24 atoms of carbon.

The N-alkylglycosylamines of Formula IV may themselves be prepared in accordance with the method of J. G. Erikson, 1955, J. Am. Chem. Soc. 77: 2839, which consists of reacting the sugar with a long-chain alkyl amine, $RNH_2$, in a mixture of ethanol and of water at 25° C. for 24 hours. The N-alkylglycosylamines are isolated by a simple filtration. The precipitate formed is recrystallized from ethanol, then lyophilized. During a second stage, the N-alkylglycosylamines of Formula IV are subjected to an acylation.

This stage of acylation consists of reacting the N-alkylglycosylamine of Formula IV with acetic anhydride in an aprotic solvent, such as, for example, dimethylformamide (DMF) or dimethylsulfoxide (DMSO), under inert atmosphere, such as, for example, under an atmosphere of nitrogen or argon, at ambient temperature, for a time of between about 12 to about 48 hours, preferably for about 24 hours.

The N-alkyl, N-acetylglycosylamines of Formula I thus obtained are in the form of white solids, which are largely soluble and stable in aqueous solution.

The NMR characteristics, the mass spectra, and the microanalyses confirm structures as corresponding to compounds of Formula I.

These derivatives may be used as surface-active agents. They may likewise have interesting properties as agents for the solubilization of proteins for isolation of membrane proteins, or, furthermore, as inducers of asymmetry in micellar systems.

The invention is illustrated further by the following examples which are not to be construed as limiting the invention in scope or spirit to the specific procedures described in them.

EXAMPLE 1

N-heptyl, N-acetylglucosylamine (a) Preparation of N-heptylglucosylamine

A solution of heptylamine (11.5 g in 50 ml of ethanol) was added to a solution containing 9 g of glucose and 35 ml of water. The reaction mixture was stirred for about 24 hours at ambient temperature. The precipitate formed was filtered and recrystallized from ethanol, then lyophilized.

There were obtained 9 g of a solid white product, the analysis of which indicated a compound of the following formula:

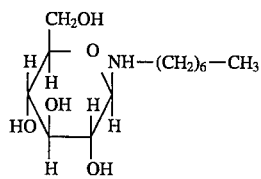

(b) Preparation of N-heptyl, N-acetylglucosylamine 1.3 g of triethylamine and 1.3 g of acetic anhydride were added, at ambient temperature, to a solution of 3.5 g of N-heptylglucosylamine in 90 ml of DMF, under argon. The reaction mixture was agitated for about 12 hours. The solvent was evaporated under vacuum. The product was washed with water, lyophilized and purified in a silicon column; elution was obtained with a chloroform/methanol/ammonia mixture (10:5:0.5).

There was obtained 1.5 g of solid product, the analyses of which indicated a compound with the following formula:

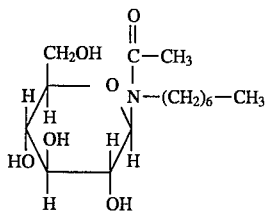

EXAMPLE 2

N-octyl, N-acetylglucosylamine (a) Preparation of N-octylglucosylamine

The process was carried out in essentially the same manner as in Example 1, but using 9 g of glucose and 13.2 g of octylamine.

There were recovered 6.5 g of a solid white product, the analysis of which indicated a product with the following formula:

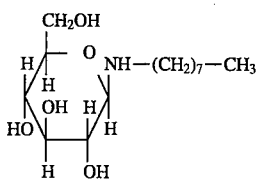

(a) Preparation of N-octyl, N-acetylglucosylamine

Essentially the same experimental protocol was utilized as in Example 1, but with 4 g of N-octylglucosylamine, 1.4 g of triethylamine, 1.4 g of acetic anhydride, and 100 ml of DMF.

There was obtained 1 g of a solid product, the analysis of which indicated a compound with the following formula:

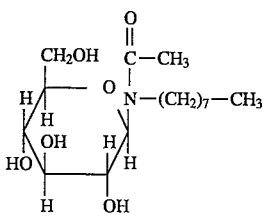

EXAMPLE 3

N-nonyl, N-acetylglucosylamine (a) Preparation of N-nonylglucosylamine

The process was carried out in essentially the same manner as in the preceding examples, using 9 g of glucose and 14.3 g of nonylamine.

There were recovered 8.8 g of a solid white product, the analysis of which indicated a product with the following formula:

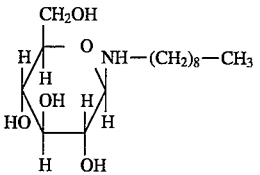

(b) Preparation of N-nonyl, N-acetylglucosylamine

The process was carried out in essentially the same manner as in the preceding examples, using 3.4 g of N-nonylglucosylamine, 1.1 g of triethylamine, 1.1 g of acetic anhydride, and 80 ml of DMF.

There was obtained 1 g of solid product, the analysis of which indicated a product with the following formula:

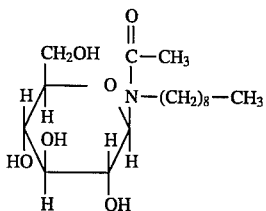

EXAMPLE 4

N-decyl, N-acetylglucosylamine (a) Preparation of N-decylglucosylamine

The process is carried out in essentially the same manner as in the preceding examples, using 9 g glucose and 15.7 g of decylamine.

There were recovered 7.5 g of solid white product, the analysis of which indicated a product with the following formula:

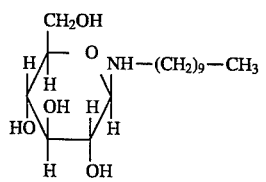

(b) Preparation of N-decyl, N-acetylglucosylamine

The process was carried out in essentially the same manner as in the preceding examples, but using 4 g N-decylglucosylamine, 1.3 g of triethylamine, 1.3 g of acetic anhydride, and 100 ml of DMF.

There were obtained 2.5 g of solid product, the analysis of which indicated a compound with the following formula

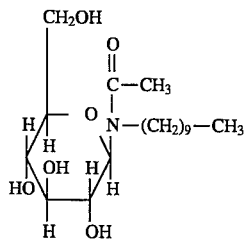

EXAMPLE 5

N-nonyl, N-acetyllactosylamine (a) Preparation of N-nonyllactosylamine

A solution of nonylamine (14.1 g) in 200 ml of 2-propanol was added to a solution containing 21 g of lactose and 120 ml of water. The reaction mixture was agitated for 24 hours at ambient temperature, then heated at 60° C. for 30 minutes.

The solvent was evaporated under reduced pressure, and the residue dissolved ethanol, then re-evaporated in the presence of toluene in order to eliminate the residual water. The final solid was recrystallized from ethanol, and then lyophilized.

There were obtained 17.6 g of a solid white product, the analysis of which indicated a compound with the following formula:

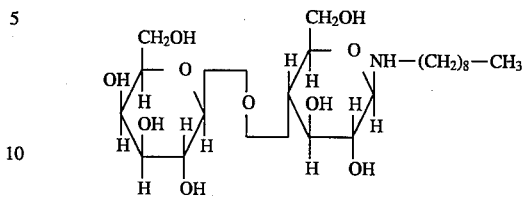

(b) Preparation of N-nonyl, N-acetyl lactosylamine

To a solution of 6 g of N-nonyllactosylamine in 80 ml of DMF under argon, there was added 1.3 g of triethylamine and 1.3 g of acetic anhydride at ambient temperature. The reaction mixture was agitated for about 12 hours. The solvent was evaporated under vacuum. The product was washed in water, lyophilized, and purified on a column of silica, by eluting with a chloroform/methanol/ammonia mixture (20:15:2).

There was recovered 3.4 g of a solid product, the analysis of which indicated a compound with the following formula:

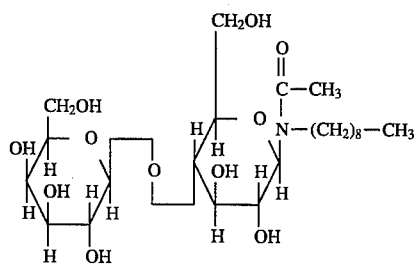

EXAMPLE 6

N-decyl, N-acetyllactosylamine (a) Preparation of N-decyllactosylamine

The process was carried out in essentially the same manner as in Step (a) of Example 5, using 21 g of lactose and 15.2 g of decylamine.

There were recovered 17.8 g of solid white product, the analysis of which indicated a product with the following formula:

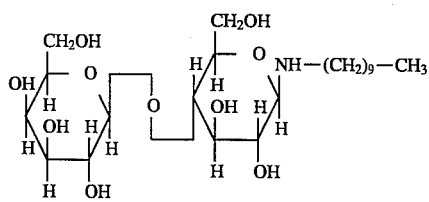

(b) Preparation of N-decyl, N-acetyllactosylamine

The process was carried out in essentially the same manner as in Step (b) of Example 5, using 10 g of N-decyllactosylamine, 2.1 g of triethylamine, 2.1 g of acetic anhydride, and 130 ml of DMF.

There were obtained 4 g of a solid product, the analysis of which indicated a compound with the following formula:

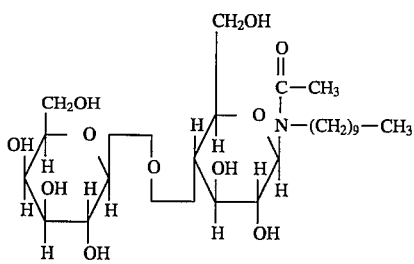

EXAMPLE 7

N-octyl, N-acetyllactosylamine (a) Preparation of N-octyllactosylamine

The process was carried out in essentially the same manner as in Examples 5 and 6 above, using 21 g of lactose and 12.8 g of octylamine.

There were recovered 16 g of a solid white product, the analysis of which indicated a product with the following formula:

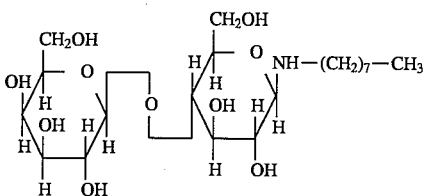

(b) Preparation of N-octyl, N-acetyllactosylamine

The process was carried out in essentially the same manner as in Examples 5 and 6 above, using 8 g of octyllactosylamine, 1.8 g of triethylamine, 1.8 g of acetic anhydride, and 110 ml of DMF.

There were obtained 3 g of a solid product, the analysis of which indicated a compound with the following formula:

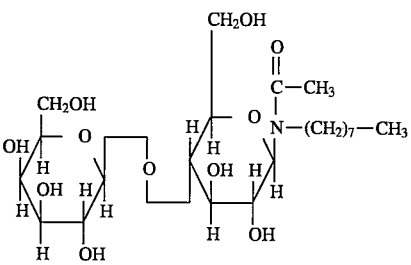

EXAMPLE 8

The surface active properties of N-decyl, N-acetylglucosylamine prepared in accordance with Example 4 can be measured by conventional techniques such as for example by using a Tensiomat N3 tensiometer (Prolabo, France). The measurements were carried out at 25° C. The measuring body was a clamp provided with a device formed with a platinum wire of 0.1 mm diameter and 2 cm length (with a gap between the 2 branches of the clamp).

The results were plotted graphically as shown in FIG. 1. From the graph, the critical micellar concentration (CMC) of N-decyl, N-acetylglycosylamine was determined to be $1.29 \times 10^3$ M/L.

What is claimed is:

1. A compound of the formula:

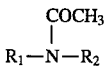

wherein $R_1$ represents the residue of a reducing sugar selected from the group consisting of glucose, galactose, lactose, and cellobiose; where the residue of a reducing sugar is attached via the anomeric carbon to the acylated nitrogen; and $R_2$ is an alkyl radical, either linear or branched, comprising from 1 to 24 atoms of carbon, with the proviso that when $R_1$ is a residue of lactose, $R_2$ is different from the nonyl radical.

2. A compound according to claim 1, which is:

wherein $R_1$ is an alkyl radical, either linear or branched, comprising 8 to 18 atoms of carbon.

3. A compound according to claim 1, which is:

wherein $R_2$ is an alkyl radical, either linear or branched, comprising 1 to 24 atoms of carbon with the proviso that $R_2$ is not a nonyl radical.

4. A compound according to claim 1, which is N-heptyl, N-acetylglucosylamine.

5. A compound according to claim 1, which is N-octyl, N-acetylglucosylamine.

6. A compound according to claim 1, which is N-nonyl, N-acetylglucosylamlne.

7. A compound according to claim 1, which is N-decyl, N-acetylglucosylamine.

8. A compound according to claim 1, which is N-nonyl, N-acetyllactosylamine.

9. A compound according to claim 1, which is N-decyl, N-acetyllactosylamine.

10. A compound according to claim 1, which is N-octyl, N-acetyllactosylamine.

* * * * *